(12) United States Patent
Kim (10) Patent No.: US 9,964,480 B2
(45) Date of Patent: May 8, 2018

(54) TEST FILM FOR DETECTING SURFACE PARTICLES IN CLEAN ROOM

(71) Applicant: JEDEX INC., Yongin-si, Gyeonggi-do (KR)

(72) Inventor: Jin Ho Kim, Suwon-si (KR)

(73) Assignee: JEDEX INC., Yongin-si, Gyeonggi-do (KR)

( * ) Notice: Subject to any disclaimer, the term of this patent is extended or adjusted under 35 U.S.C. 154(b) by 0 days. days.

(21) Appl. No.: 15/520,528

(22) PCT Filed: Jul. 3, 2015

(86) PCT No.: PCT/KR2015/006847
§ 371 (c)(1),
(2) Date: Apr. 20, 2017

(87) PCT Pub. No.: WO2016/064067
PCT Pub. Date: Apr. 28, 2016

(65) Prior Publication Data
US 2017/0315038 A1 Nov. 2, 2017

(30) Foreign Application Priority Data

Oct. 22, 2014 (KR) ........................ 10-2014-0143564

(51) Int. Cl.
*G01N 15/02* (2006.01)
*G01N 21/88* (2006.01)
(Continued)

(52) U.S. Cl.
CPC ........... *G01N 15/0205* (2013.01); *G01N 1/04* (2013.01); *G01N 1/20* (2013.01); *G01N 21/8803* (2013.01); *G01N 2001/028* (2013.01)

(58) Field of Classification Search
CPC ......... G01N 15/0205; G01N 1/04; G01N 1/20
(Continued)

(56) References Cited

U.S. PATENT DOCUMENTS 5,690,749 A * 11/1997 Lee ..................... B08B 7/0028
134/26
2015/0276205 A1* 10/2015 Cai ..................... F21V 33/0064
362/147

FOREIGN PATENT DOCUMENTS

JP      2002-142797 A    5/2002
JP      2007-135476 A    6/2007
(Continued)

*Primary Examiner* — Roy M Punnoose
(74) *Attorney, Agent, or Firm* — Novick, Kim & Lee, PLLC; Jae Youn Kim (57) ABSTRACT

The present invention relates to a test film for detecting surface particles in a clean room in order to prevent inferior products by measuring the contamination level of the clean room using the surface particles. The present invention provides a test film for detecting surface particles in a cleanroom, the test film comprising a substrate which has a predetermined thickness and is formed of a transparent synthetic resin material; a first adhesive layer which is formed at one side of the substrate and collects the surface particles; a release film which is adhered to the first adhesive layer and is separated from the first adhesive layer when the surface particles are collected; a second adhesive layer which is formed at the other side of the substrate; and a protective film which is adhered to the second adhesive layer so as to protect the substrate and has gradations indicated thereon. According to the present invention, there is an effect in that it is possible to easily and quickly check whether or not a clean room is contaminated by collecting, on the adhesive layer-applied surface of a substrate to which an adhesive is applied, surface particles adhered to an object to be measured, and then measuring the number, size, distribution, etc. of the surface particles with the naked eye or using instruments such as a light, a magnifier, a microscope, or the like.

8 Claims, 13 Drawing Sheets

(51) Int. Cl.
*G01N 1/04* (2006.01)
*G01N 1/20* (2006.01)
*G01N 1/02* (2006.01)

(58) Field of Classification Search
USPC ..................................................... 356/239.8
See application file for complete search history.

(56) References Cited

FOREIGN PATENT DOCUMENTS

| | | |
|---|---|---|
| JP | 2014-048100 A | 3/2014 |
| KR | 10-0567789 B1 | 4/2006 |
| KR | 20-0462481 Y | 9/2012 |
| KR | 10-1264075 B1 | 5/2013 |

* cited by examiner

TEST FILM FOR DETECTING SURFACE PARTICLES IN CLEAN ROOM

TECHNICAL FIELD

The present invention relates to a test film for detecting surface particles in a clean room, more particularly, a test film for detecting surface particles in a clean room in order to prevent product defect by measuring the contamination level by the surface particles in the clean room.

BACKGROUND ART

Generally, as the industry is getting sophisticated, there is an increasing need to control particles such as dust and the like in production sites as well as in office environments, and thus a clean room was introduced to keep the production site clean at all times and thus to prevent adverse effects on the product by the particles.

Such a clean room refers to a space where contamination control is performed by controlling the concentration of the particles floating in the air within a indicated cleanliness level limit, wherein the space is also controlled and managed for environmental conditions such as temperature, humidity, room pressure, illuminance, noise, and vibration, if necessary. These clean rooms are currently being installed and operated in various industries including semiconductors, LCD displays, aviation, pharmaceuticals, hospitals, food and the like.

Especially, in the high-tech industry including a highly precise process at nano-level such as a semiconductor manufacturing process, a LCD display manufacturing process and the like, since minute environmental conditions at the site where the product is manufactured can also have a great influence on the quality of the product, the cleanliness which is required in the clean room is getting stronger. For example, in the semiconductor manufacturing process, it is pointed out that pattern defects caused by deposition of particles oscillated from an automation device or the like on the surface of the wafer are the main causes of the yield reduction of the product.

As such, if the particles are present at the site where the product is manufactured, the particles may be transferred to the product during the manufacturing process and thus may cause fatal product defect. These particles are accumulated on ceilings, walls, floors, production and measurement equipment, various equipment and the like of the site where the product is manufactured, and are attached to the surface of the worker's clothing, and when causing the movement of airflow due to the movement of robots, workers and products, and the spatial imbalance of temperature, the surface particles accumulated on the surface of workers, objects, or their adjacent portions will be transferred to contaminate the product, thereby causing product defect.

In general, a method for collecting the suspended particles in the air with a filter paper is used, but since these particles in the clean room are usually very small in diameter and may not be visible to the naked eye, a separate particle detector for measuring contaminants in the clean room is used, and then, by using this particle detector, the particle distribution state in a specific chamber of a facility is being measured in real time.

As a specific prior art, Korean Patent Registration No. 10-0567789 (published on Apr. 5, 2006) discloses a particle measuring device consisting of a particle charging mean for charging particles; an internal guide duct through which clean air is introduced; an electrode which is installed longitudinally in the internal guide duct; a plurality of particle separators which are located outside the internal guide duct, which are longer than the length of the internal guide duct, and into which particles charged by a particle charging mean located between with the internal guide duct are entered, and which are provided with an external guide duct having a particle collection portion at the downstream; a power supply mean for providing different power sources such that a voltage difference is occurred at each electrode of a plurality of particle separators; and a plurality of particle counting means for measuring the number of particles collected by the particle separators.

In addition, as another prior art, Korean Patent Registration No. 10-1264075 (published on May 13, 2013) discloses an optical particle measuring device characterized in that the device comprises a suction portion through which air is sucked into a measurement space; a measurement chamber having an outlet through which air passed through the interior of the measurement space is discharged; a plurality of light source portions adapted to illuminate the interior of the measurement space of the measurement chamber with light having different wavelengths; a plurality of photo-detection portions for detecting light which is irradiated from a plurality of light sources respectively and is scattered by the particles contained in the air passing through the interior of the measurement space, and thus generating an electrical signal corresponding to the amount of light therefrom; a light removal portion for removing light which is irradiated from a plurality of light sources respectively and is not scattered by the particles; a plurality of computation portions for calculating the particle size distribution and the number of particles by size from the magnitude and frequency of the electrical signals detected respectively by a plurality of photo-detection portions; and a plurality of mirrors which are disposed one by one on the opposite side of each of a plurality of photo-detection portions and can reflect the scattered light toward the corresponding photo-detection portions, wherein a plurality of mirrors are arranged such that the lights reflected by a plurality of mirrors do not overlap with each other and a plurality of light source portions simultaneously irradiate light having different wavelengths into the interior of the measurement space.

However, since the above-described prior arts require to separately purchase an expensive particle measuring device for particle measurement, there is a problem not only that a lot of cost is required, but also that the operation of the equipment is complicated, a long time is required for inspection, and a large space is required because of the large size of the equipment.

Also, particle measuring devices according to the above-described prior art can measure the number, size, or distribution of the whole particles in the clean room, but there is a problem in that it is difficult to identify the sampled specimen and it is impossible to judge from which object the collected particles are generated, and to judge the place where the object entered along with a large amount of particles is located, and thus it is difficult to control contamination by particles in the clean room.

In addition, although there is a method of cleaning the surface of the object to be measured with clean water and then counting the particles with a counter for counting particles in the liquid, there is a problem in that it is difficult to detect particles which are dissolved in water and liquefied because the particles are washed with water and detected in water.

DISCLOSURE

Technical Problem

The present invention has been made in order to solve all the above-mentioned problems, and thus it is an object of the present invention to provide a test film for detecting surface particles in a clean room, which can easily and quickly check whether or not the clean room is contaminated, by collecting surface particles adhered to the object to be measured on the adhesive layer-applied surface of a substrate to which adhesive is applied, and then measuring the number, size, distribution, etc. of the surface particles with the naked eye or using instruments such as a magnifier, a microscope, or the like.

Technical Solution

In order to solve the above problems, the present invention provides a test film for detecting surface particles in a clean room, comprising a substrate which has a predetermined thickness and is formed of a transparent synthetic resin material; a first adhesive layer which is formed on one side of the substrate and collects the surface particles; a release film which is adhered to the first adhesive layer and is separated from the first adhesive layer when the surface particles are collected; a second adhesive layer which is formed on the other side of the substrate; and a protective film which is adhered to the second adhesive layer so as to protect the substrate and has gradations indicated thereon.

At this time, the present invention is also characterized in that the substrate can be made of a hard synthetic resin.

Furthermore, the present invention is also characterized in that the substrate can be made of any one selected from polycarbonate (PC), polymethyl methacrylate (PMMA), polyethylene (PE), polyethylene terephthalate (PET) and polystyrol (PS).

In addition, the present invention is also characterized in that the substrate can include a body portion, a grip portion formed on one end of the body portion, and an incision portion formed between the body portion and the grip portion, wherein the release film can be easily separated while gripping the grip portion by hand.

Moreover, the present invention is also characterized in that in the state in which the release film is separated, the surface particles can be adhered to and collected on the first adhesive layer, and then the separated release film can be reattached to the first adhesive layer again.

Here, the present invention is also characterized in that it is possible to determine whether or not a clean room is contaminated by counting the number of bubbles generated in the release film due to the collected surface particles or checking the size of the bubbles, In addition, the present invention is also characterized in that the protective film may be detachably attached to the second adhesive layer, thereby being possible to separate the protective film or attach another protective film to the second adhesive layer.

In addition, the present invention is also characterized in that a color film having a color may be adhered on the protective film.

Advantageous Effects

According to the present invention, there is an effect in that it is possible to easily and quickly check whether or not a clean room is contaminated by collecting the surface particles adhered to an object to be measured on the adhesive layer-applied surface of a substrate to which adhesive is applied, and then measuring the number, size, distribution, etc. of the surface particles with the naked eye or using instruments such as a magnifier, a microscope, or the like.

In addition, the present invention has an effect in that it is easy to confirm the sampled specimen, it is possible to judge from which object the surface particles have been detected, and it is possible to maintain the clean room in a super clean state by measuring the number, distribution, etc. of the surface particles collected from a specific object to be measured, and then detecting the place where a large amount of surface particles has been introduced, and thereafter appropriately controlling contamination by the surface particles in the clean room.

In addition, the present invention has an effect in that accurate measurement is possible during microscopic inspection since the substrate is made of a material that does not bend well, the release film is detachably attached to the adhesive layer so that, at ordinary time, the adhesive layer-applied surface is protected from particles that are not to be tested, and then, at the time of collecting the particles, the release film is separated, and after collection of the particles, the release film is reattached to the adhesive layer, thereby preventing contamination of the sampled specimen when moving it to the inspection apparatus or the inspection site, as well as it is possible to easily determine whether or not the clean room is contaminated, by checking the number or size of bubbles generated on the surface.

In addition, the present invention has an effect in that, by forming the protective film on the substrate, contamination of the substrate or formation of scratches, etc. in the course of operations such as printing, movement, circulation and cutting, etc. of the test film can be prevented, and the protective film having gradations indicated thereon can be easily separated or replaced with the other protective film having gradations indicated thereon

BEST MODE FOR THE INVENTION

Hereinafter, a detailed description for implementing the test film for detecting the surface particles of the clean room according to the present invention will be described in detail by exemplifying embodiments with reference to the drawings.

According to a report on "Research on Development of Super Clean Room of Class 1" issued by the Ministry of Science and Technology in October 1992, it is generally known that adhesion of particles occurred in a clean room to the surface is the most important matter in view of contamination control in a clean room, wherein the particles floating in the air in the clean room reach very close to the surface due to Brownian diffusion, turbulent diffusion, external force and the like, and at this time, the potential energy exists and the particles have a minimum energy in the immediate vicinity of the surface of the object to be measured by Van der Waals force or the like, and in general, when the minimum value of this energy ($\varphi$) is smaller than 20 kT, the particles are adhered to positions of $\sigma$(0.001 µm or less).

As such, it is known that the main adhesion force between the particles and the surface of the object to be measured includes Van der Waals force, electrostatic force, and surface tension along the liquid surface, and since the fine particles in the clean room have a large surface area compared to their volume, they tend to adhere strongly to the contact surface of the object to be measured.

Figure 1:
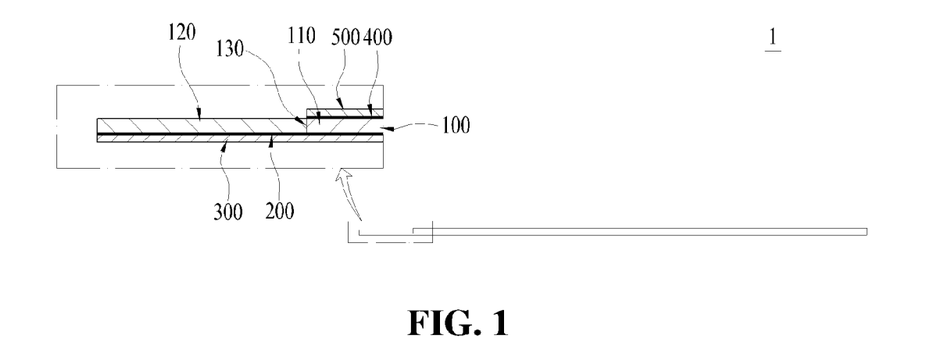
FIG. 1 is a view showing the structure of a test film according to one embodiment of the present invention.
Figure 2:
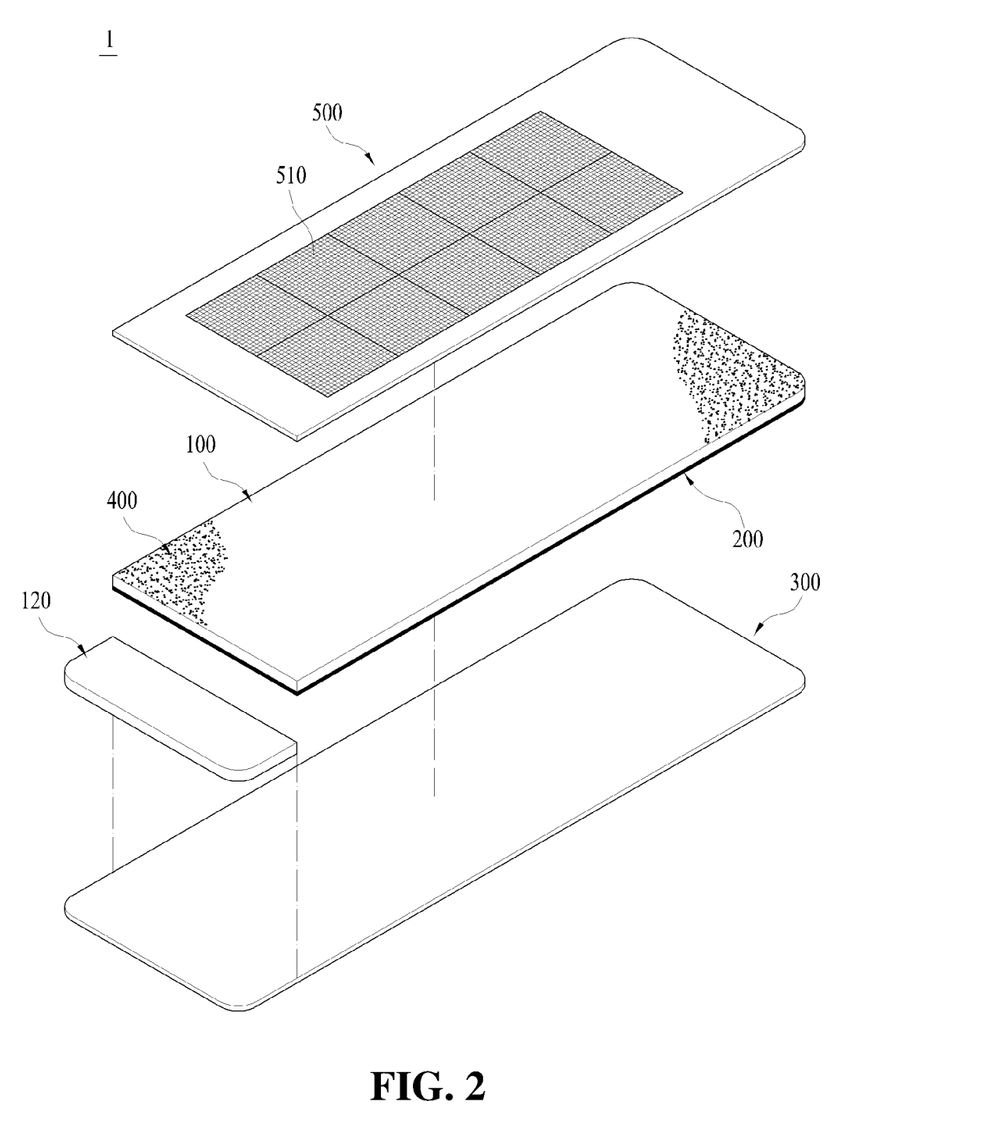
FIG. 2 is an exploded perspective view of a test film according to an embodiment of the present invention.

Now, referring to FIG. 1 and FIG. 2, the test film 1 for detecting surface particles in a clean room according to the present invention is intended to prevent product defect by measuring the degree of contamination by the surface particles in the clean room, wherein the test film includes a substrate 100, a first adhesive layer 200, a release film 300, a second adhesive layer 400, and a protective film 500, thereby being possible to easily and conveniently check whether or not the clean room is contaminated and to control contamination, by collecting, on the applied surface of the first adhesive layer 200 of the substrate 100 to which adhesive was applied, the surface particles P adhered to the object to be measured, and then measuring the number, size, distribution, etc. of the surface particles P with the naked eye or using instruments such as a light, a magnifier, a microscope, or the like.

For this, the substrate 100 has a predetermined thickness larger than those of the release film 300 or the protective film 500 so that the substrate is not curved or bent and acts like a slide glass during microscopy, and therefore it is possible to accurately measure the number, size, and distribution of the surface particles P collected on the first adhesive layer 200.

For this, the substrate 100 is preferably made of a hard synthetic resin having a predetermined hardness, and for example, can be made of any one selected from polycarbonate (PC), polymethyl methacrylate (PMMA), polyethylene (PE), polyethylene terephthalate (PET) and polystyrol (PS).

In addition, since the substrate 100 is made of a transparent synthetic resin material having translucency, the surface particles P adhered to the first adhesive layer 200 and thus collected thereon can be easily observed with the naked eye or using instruments such as a light, a magnifier, or a microscope.

The first adhesive layer 200 is formed by applying adhesive to one side of the substrate 100, the release film 300 is detachably attached to the first adhesive layer, and the surface particles are collected by adhering the surface particles accumulated on or adhered to the surface of the object such as ceilings, walls and floors of the clean room, production and measurement equipment, various applications and workers' clothing, etc., to the exposed surface applied with the first adhesive layer 200, which is exposed by separating a part or all of the release film 300

In addition, the number, size, or distribution, etc. of the surface particles P can be measured with the naked eye or using instruments such as a light, a magnifier or a microscope, and thus the number of the surface particles P can be quantified, and a criterion of judgment for a specific test purpose can be introduced and established.

Therefore, it is easy to confirm the sampled specimen, it is possible to judge from which object the surface particles P have been collected, and a super clean room state of class 1 can be maintained by measuring the number and distribution of the surface particles P collected from a specific object and determining the place where a large amount of surface particles has been introduced, and thereafter appropriately controlling contamination by the surface particles (P) in the clean room.

The release film 300 is detachably attached to the first adhesive layer 200, and when collecting the surface particles P from the object to be measured, the release film is separated from the first adhesive layer 200.

At this time, the substrate 100 includes a body portion 110 having a flat shape, a grip portion 120 which is formed at one end of the body portion 110 and gripped by a user's hand at the time of separating the release film 300, and an incision portion 130 which is formed by making an incision between the body portion 110 and the grip portion 120 to facilitate the separation of the release film 300.

Figure 3:
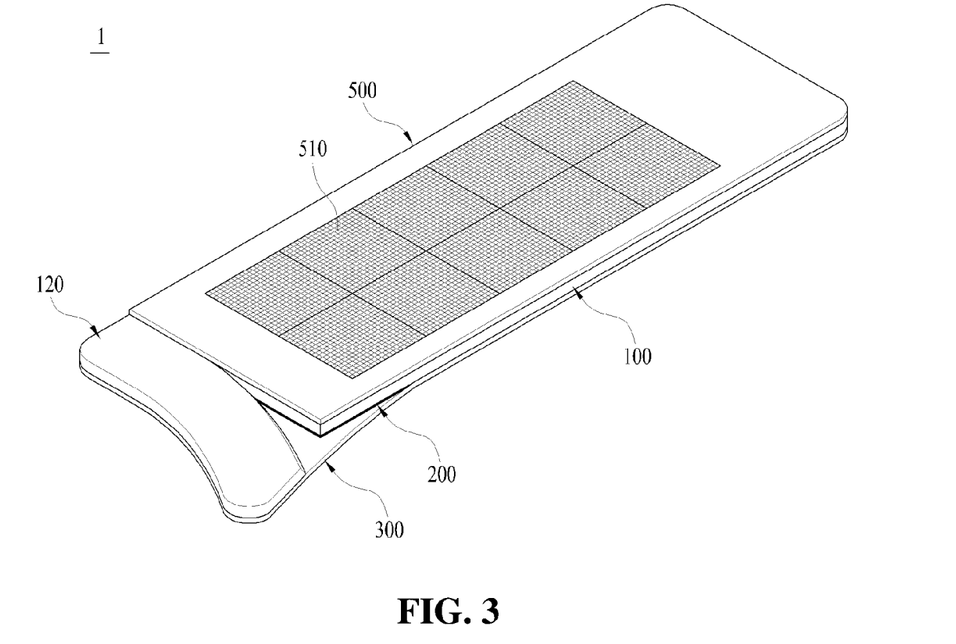
FIG. 3 is a view showing a process of separating a release film from a test film according to an embodiment of the present invention.

Therefore, referring to FIG. 3, the user can hold the grip portion 120 by hand and then easily separate the release film 300, as well as foreign matters other than the surface particles P from the object to be measured are prevented from adhering to the applied surface of the first adhesive layer 200, so that the accuracy of detection can be increased.

In addition, in order to collect the surface particles P, the surface particles P are adhered to and collected on the applied surface of the first adhesive layer 200 in the state in which a part or all of the release film 300 is separated, and then the separated release film 300 is reattached to the first adhesive layer 200 again.

Therefore, since the release film 300 is detachably attached to the first adhesive layer 200, at ordinary time, the applied surface of the first adhesive layer 200 is prevented from being contaminated, and at the time of collecting the surface particles P, the release film 300 is separated and after removal and collection of the surface particles P from the object to be measured, the release film 300 is reattached to the first adhesive layer 200 to prevent the sampled specimen from being contaminated when the test film 1 is moved to the inspection apparatus or the inspection site, thereby obtaining accurate measurement results.

Figure 4:
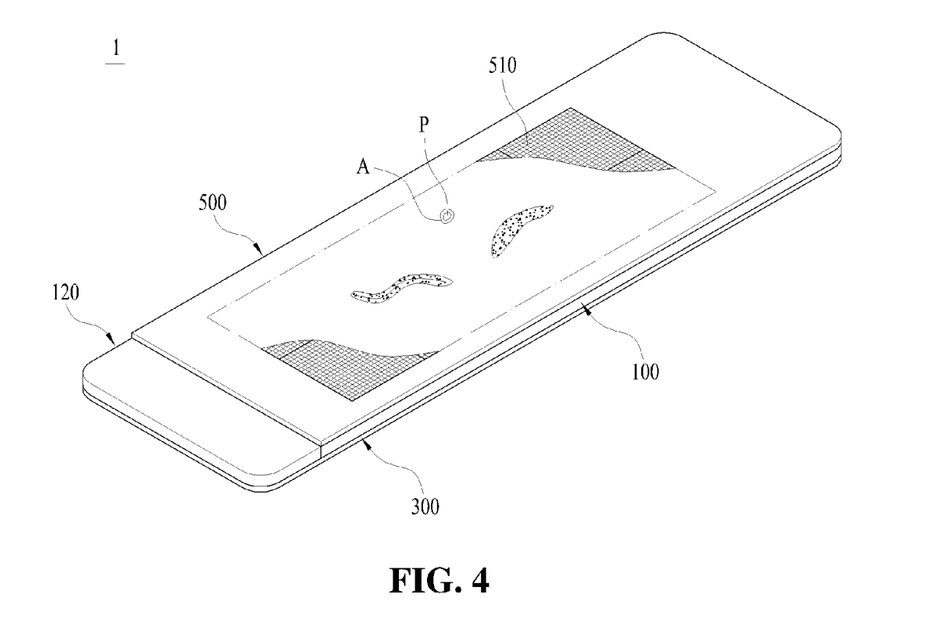
FIG. 4 is a view showing a process of collecting particles on a test film according to an embodiment of the present invention, reattaching the separated release film, and checking the generated bubbles, thereby determining whether or not contamination has occurred.

Moreover, referring to FIG. 4, after separation of the release film 300 and collection of the surface particles P on the applied surface of the first adhesive layer 200, if the release film 300 is reattached to the first adhesive layer 200, bubbles A are generated inside the release film 330 at the position to which the collected surface particles P are attached, so that the presence or not of contamination and the degree of contamination can be easily determined by counting the number of the bubbles A generated in the release film 300 or checking the size of the bubbles A with the naked eye.

The second adhesive layer 400 is formed by applying adhesive to the other side of the substrate 100, the protective film 500 is detachably attached to the second adhesive layer 400 to protect the substrate 100, and the protective film 500 has gradations 510 indicated thereon.

Accordingly, if it is necessary to confirm the presence or not of contamination by the surface particles P as a whole, the protective film 500 may be separated from the second adhesive layer 400, and the protective film 500 having various gradations 510 of different sizes may alternatively be attached to the second adhesive layer 400.

Figure 5:
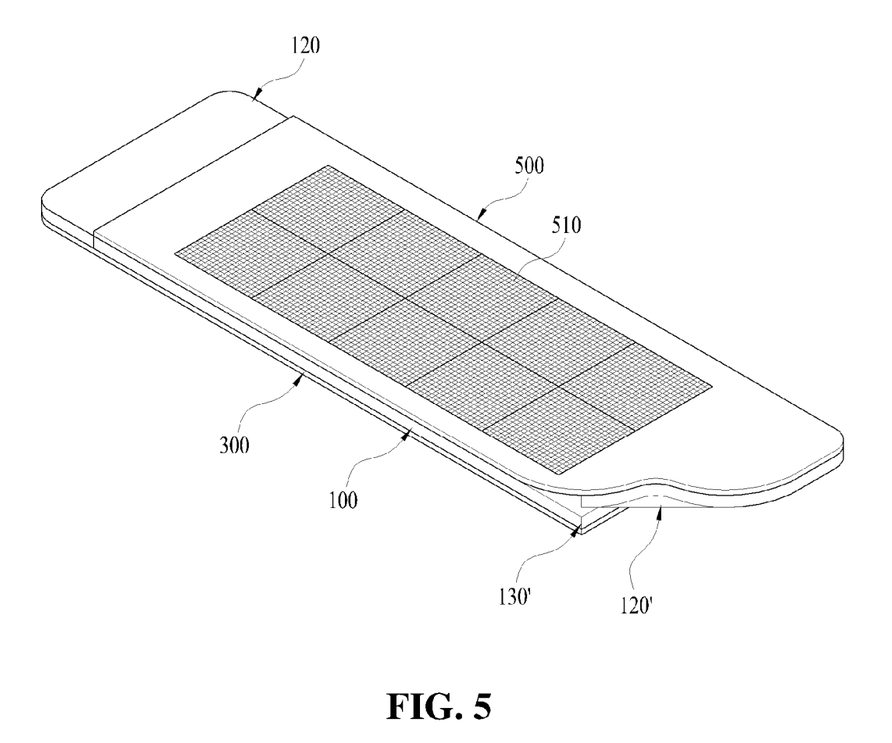
FIG. 5 is a view showing a process of separating a protective film from a test film according to an embodiment of the present invention.

At this time, the substrate 100 can include a body portion 110 having a flat shape, a grip portion 120' which is formed on the other end of the body portion 110 and gripped by a user's hand at the time of separating the release film 300, and an incision portion 130' which is formed between the body portion 110 and the grip portion 120' to facilitate the separation of the release film 300.

Therefore, referring to FIG. 5, the user can easily separate the protective film 500 while gripping the grip portion 120' formed at the other end of the body portion 110 by hand.

As such, it is possible to prevent contamination of the substrate 100 or formation of scratches, etc. in the course of operations such as printing, movement, circulation and cutting, etc. of the test film 1 by forming the protective film 500 on the substrate 100, and there is an effect in that the protective film 500 having gradations 510 indicated thereon can be easily separated or can be replaced with another protective film 500 having gradations indicated thereon.

Figure 6:
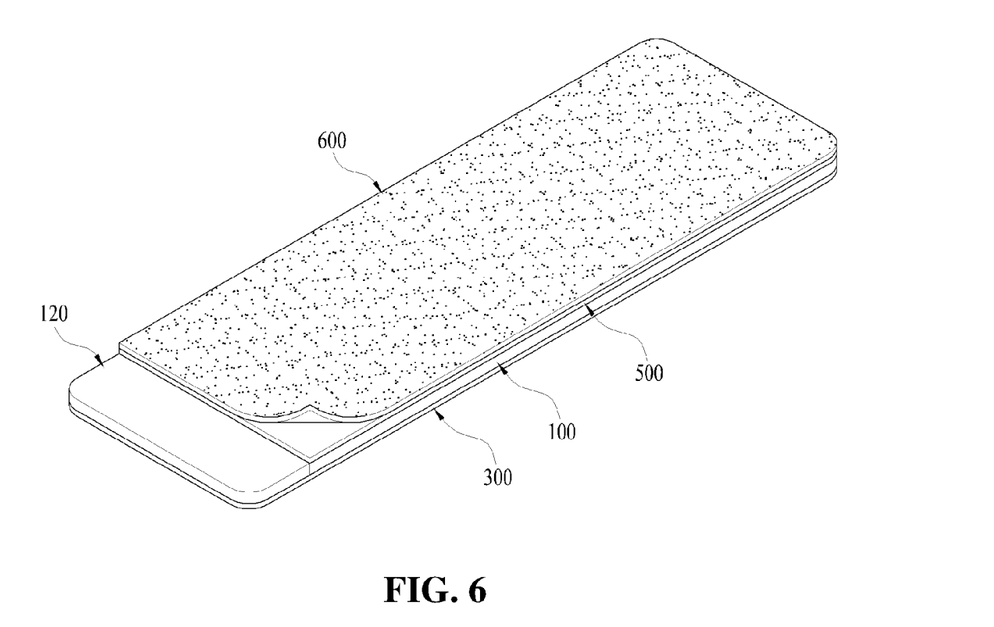
FIG. 6 is a view showing the structure of a test film according to another embodiment of the present invention.

Furthermore, referring to FIG. 6, a color film 600 having a predetermined color may be attached on the protective film 500, and the collected surface particles P can be more easily confirmed with the optical mechanism or the reflected light by attaching the color film 600 having a color of, for example, blue or black.

FIGS. 7a to 7g as examples show photographs in which the surface particles are detected using a test film according to an embodiment of the present invention.

Figure 7A:
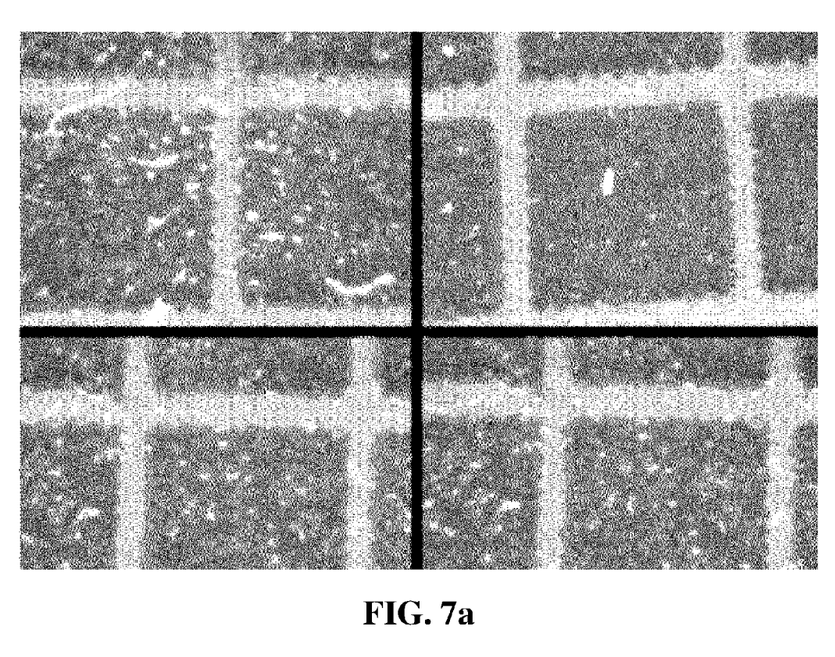
FIGS. 7a to 7g are photographs showing surface particles detected by a test film according to an embodiment of the present invention.
Figure 7B:
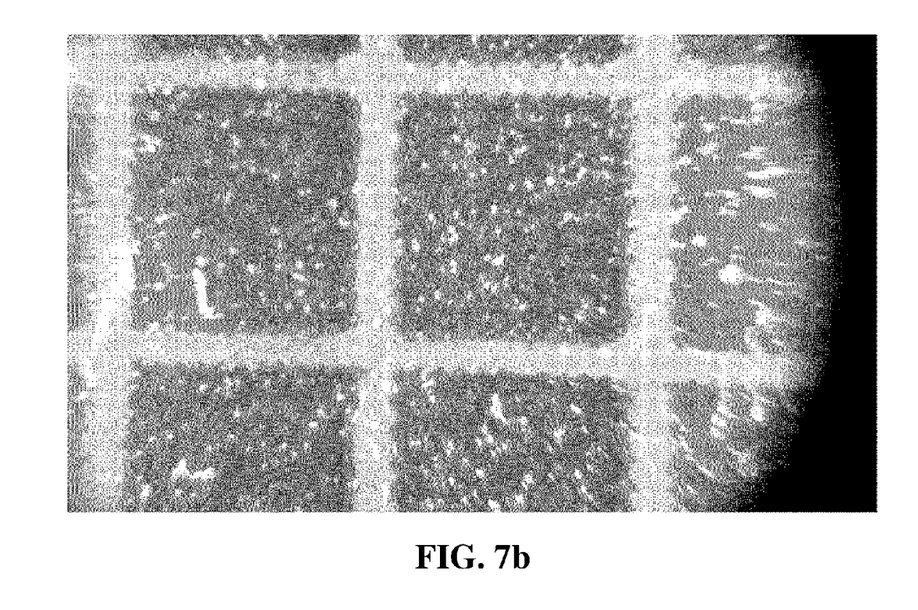
Figure 7C:
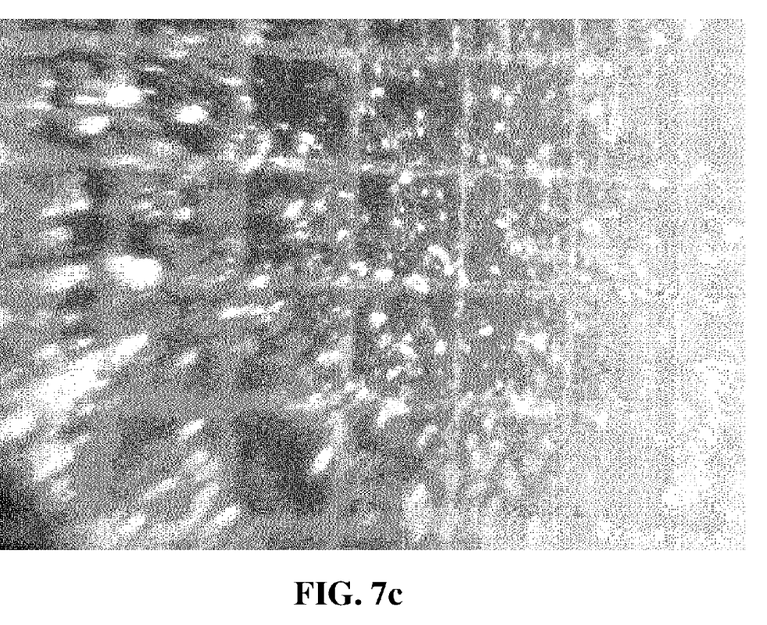

More specifically, FIG. 7a shows a microscope detection photograph of the surface particles collected from the surface of a mouse pad by using a test film with gradation interval of 2 mm, FIG. 7b shows a microscope detection photograph of the surface particles collected from the surface of a mouse pad by using a test film with gradation interval of 1 mm, and FIG. 7c is a microscope detection photograph of the surface particles collected from the skin of human face by using a test film with gradation interval of 0.5 mm. It can be confirmed from the above-mentioned Figs that although the sizes of the surface particles are small, the numbers of surface particles are large and the distributions per unit area are dense, and thus the degrees of cleanliness are low.

Figure 7D:
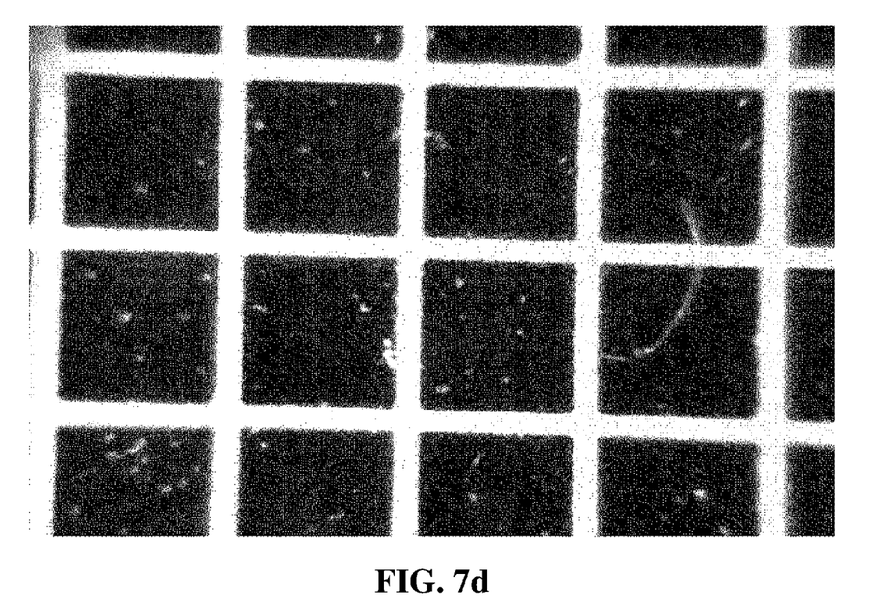
Figure 7E:
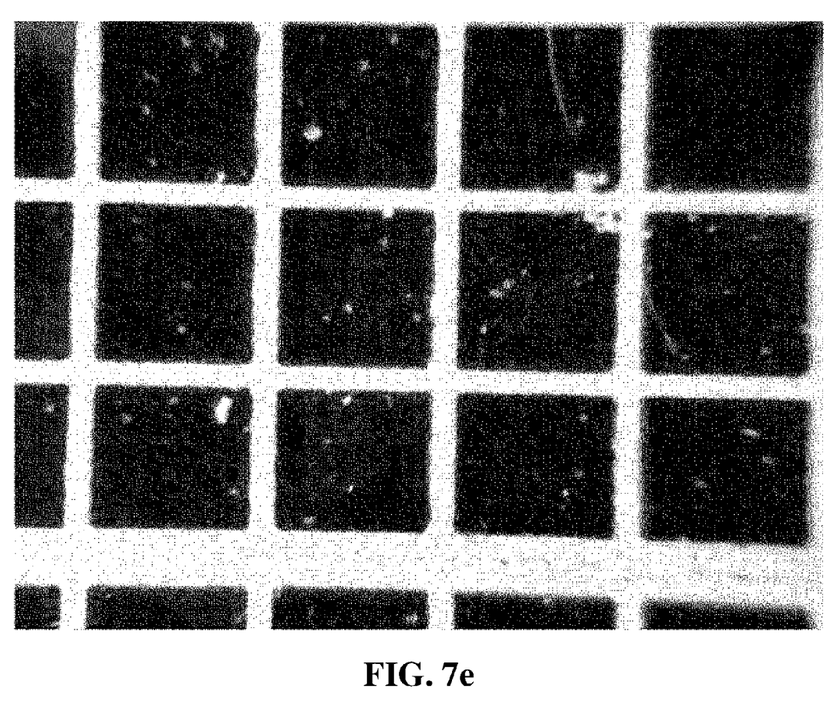
Figure 7F:
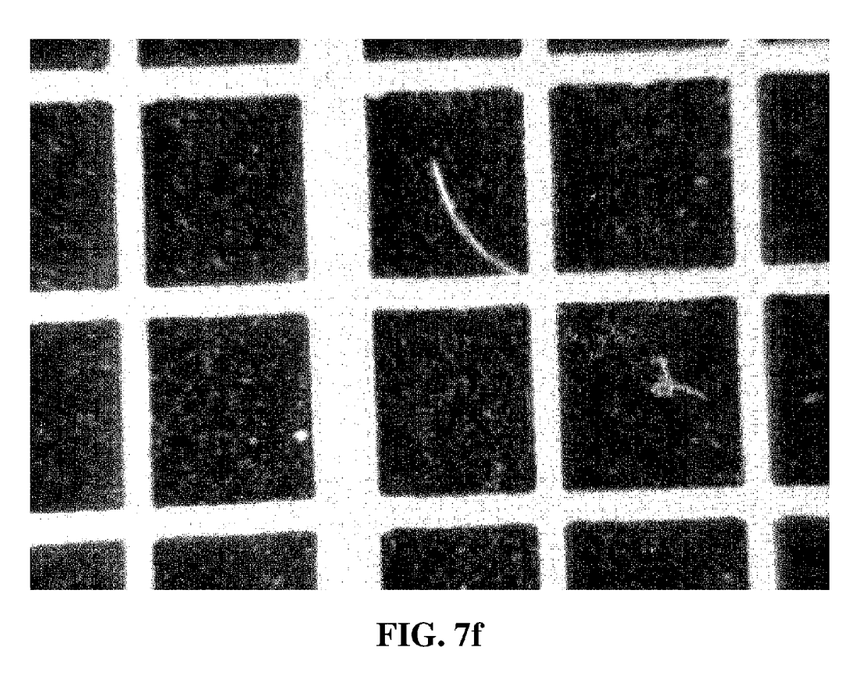

In addition, FIG. 7d is a microscope detection photograph of the surface particles collected from the surface of an object used in a clean room by using a test film with gradation interval of 1 mm, FIG. 7e is a microscope detection photograph of the surface particles collected by placing a wafer produced in the clean room on the first adhesive layer of the test film with gradation interval of 1 mm and tapping the wafer, and FIG. 7f is a microscope detection photograph of the surface particles removed from a gown worn by a worker in a clean room by using a test film with gradation interval of 1 mm. It can be confirmed from the above-mentioned Figs that since the surface particles in the case of FIGS. 7d to 7f are collected inside the clean rooms, the numbers of the surface particles are smaller than in the case of FIGS. 7a to 7c and the distributions per unit area are dispersed, and thus the degrees of cleanliness are high, but the above clean rooms need strict contamination control because they did not reach a super clean room state.

Figure 7G:
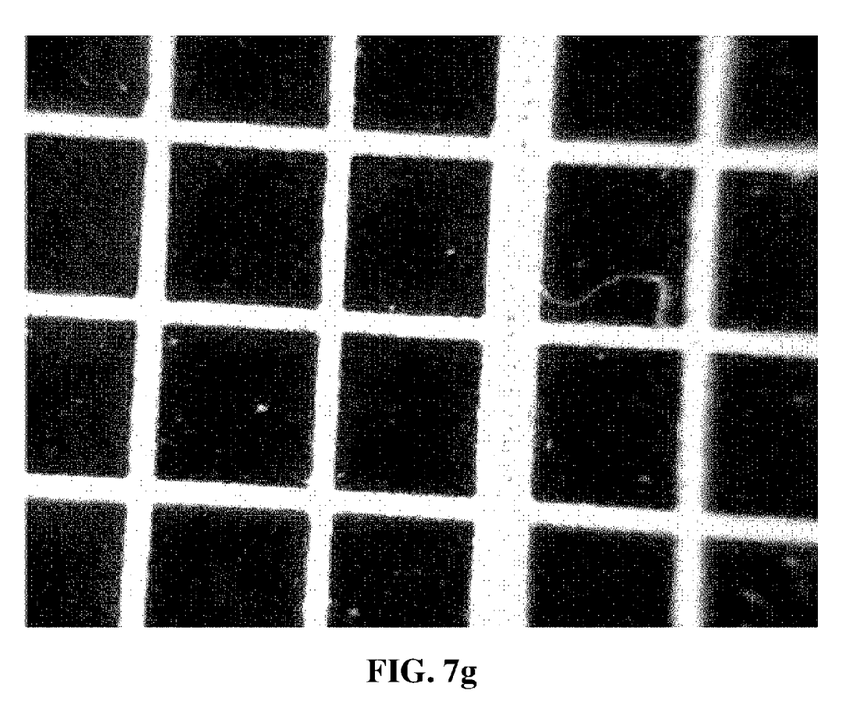

FIG. 7g is a microscope detection photograph of the surface particles collected from the surface of the wafer produced in a clean room by using a test film with gradation interval of 1 mm after cleaning the wafer. It can be confirmed from the above-mentioned Fig that it has a very good cleanliness in comparison with the case of FIGS. 7a to 7f, but since the detected surface particles having a size of about 1 mm can be deposited on the surface of the wafer and thus there is a possibility of product defect, it is necessary to find out the object on which surface particles are generated and to control contamination appropriately.

Consequently, the test film 1 for detecting the surface particles in a clean room according to the present invention can easily and quickly confirm whether or not contamination has been occurred by collecting the surface particles adhered to the object to be measured on the adhesive layer-applied surface of the substrate to which adhesive was applied, and then measuring the number, size, and distribution of the surface particles with the naked eye or using instruments such as a magnifier or a microscope. In addition, the test film 1 is easy to identify the sampled specimen and make it possible to judge from which object the collected surface particles were detected, and therefore, the clean room can be maintained in a super clean room state by measuring the number and distribution of the surface particles collected from a specific object to be measured, detecting the place where a large amount of surface particles has been introduced, and then appropriately controlling contamination by the surface particles in the clean room. Moreover, since the substrate is made of a material that does not bend well, when using a microscope, accurate measurements are possible. In addition, the release film is detachably attached to the adhesive layer, and therefore, at ordinary time, the applied surface of the adhesive layer is protected from particles not to be inspected and at the time of collecting the surface particles, the release film is separated and, after collection of the surface particles, the release film is reattached to the adhesive layer to prevent the sampled specimen from being contaminated when moving it to the inspection apparatus or the inspection site, as well as the presence or not of contamination can be easily determined by checking the number or size of bubbles generated on the surface. In addition, it is possible to prevent contamination of the substrate or formation of scratches, etc. in the course of operations such as printing, movement, circulation and cutting, etc. of the test film by forming the protective film on the substrate, and it will be possible to easily separate the protective film indicated by the gradations or to replace with another protective film having gradations indicated thereon The above-described embodiments of the present invention are merely illustrative and are not intended to limit the present invention. Technical ideas whatever having substantially the same constitution as that described in the claims of the present invention and achieving the same operational effect as that described in the claims are included in the technical scope of the present invention.

INDUSTRIAL APPLICABILITY

The test film for detecting surface particles in a clean room according to the present invention can be used to easily and quickly check whether or not the clean room is contaminated, by collecting the surface particles attached to the object to be measured on the adhesive layer-applied surface of the substrate applied with the adhesive, and then measuring the number, size, and distribution of the surface particles with the naked eye or using instruments such as a magnifier or a microscope, and thus has industrial applicability.

The invention claimed is:

1. A test film for detecting surface particles in a clean room, comprising a substrate which has a predetermined thickness and is formed of a transparent synthetic resin material; a first adhesive layer which is formed on one side of the substrate and collects the surface particles; a release film which is attached to the first adhesive layer and is separated from the first adhesive layer when the surface particles are collected; a second adhesive layer which is formed on the other side of the substrate; and a protective film which is attached to the second adhesive layer so as to protect the substrate and has gradations indicated thereon.

2. The test film for detecting the surface particles in the clean room according to claim 1 characterized in that the substrate is formed of a hard synthetic resin.

3. The test film for detecting the surface particles in the clean room according to claim 2 characterized in that the substrate is formed of any one selected from polycarbonate (PC), polymethyl methacrylate (PMMA), polyethylene (PE), polyethylene terephthalate (PET), and polystyrol (PS).

4. The test film for detecting the surface particles in the clean room according to claim 1 characterized in that the substrate includes a body portion, a grip portion formed at one end of the body portion, and an incision portion formed between the body portion and the grip portion, and the release film can be easily separated while gripping the grip portion.

5. The test film for detecting the surface particles in the clean room according to claim 1 characterized in that, in the state in which the release film is separated, the surface particles are adhered to and collected on the first adhesive layer, and then the separated release film is reattached to the first adhesive layer again.

6. The test film for detecting the surface particles in the clean room according to claim 5 characterized in that it is possible to determine whether or not a clean room is contaminated by counting the number of bubbles generated in the release film due to the collected surface particles or checking the size of the bubbles.

7. The test film for detecting the surface particles in the clean room according to claim 1 characterized in that the protective film is detachably attached to the second adhesive layer, thereby being possible to separate the protective film or attach another protective film to the second adhesive layer.

8. The test film for detecting the surface particles in the clean room according to claim 1 characterized in that a color film having a color is attached on the protective film.

* * * * *